United States Patent [19]
Patterson et al.

[11] Patent Number: 5,888,765
[45] Date of Patent: Mar. 30, 1999

[54] ENDOTHELIAL-CELL SPECIFIC PROMOTER

[75] Inventors: Winston Campbell Patterson, Brighton; Mu-En Lee, Newton, both of Mass.; Edgar Haber, Salisbury, N.H.

[73] Assignee: President and Fellows of Harvard College, Cambridge, Mass.

[21] Appl. No.: 494,282

[22] Filed: Jun. 23, 1995

[51] Int. Cl.$^6$ .......................... C12N 15/09; C12N 15/11; C12N 15/79; C12N 15/85
[52] U.S. Cl. .................. 435/69.1; 435/172.3; 435/320.1; 435/325; 536/24.1; 536/23.1
[58] Field of Search .................................. 435/69.1, 325, 435/320.1, 172.3; 536/24.1, 23.1

[56] References Cited

FOREIGN PATENT DOCUMENTS

| | | | |
|---|---|---|---|
| WO 92/13063 | 8/1992 | WIPO | C12P 21/00 |
| WO 94/10202 | 5/1994 | WIPO | C07K 15/00 |
| WO 94/11499 | 5/1994 | WIPO | C12N 15/12 |

OTHER PUBLICATIONS

Kolch, et al., "Regulation of the expression of the VEGF/VPS and its receptors: role in tumor angiogenesis" *Breast Cancer Research and Treatment* (1995) 36: 139–155.

Patterson et al., "Cloning and Functional Analysis of the Promoter for KDR/flk-1, a Receptor for Vascular Endothelial Growth Factor", *J. Biol. Chem.*, 270:23111–118, 1995.

Schlaeger, et al., "Vascular endothelial cell lineage-specific promoter in transgenic mice", *Development* vol. 121, pp. 1089–1098.

Orkin et al. "Report and Recommendation of the Panel to Assess the NIH Investment in Research on Gene Therapy", issued by the National Institutes of Health, Dec. 7, 1995.

Spritz et al., "A YAC contig spanning a cluster of human type III receptor protein tyrosine kinase genes (PDGFRA––KIT–KDR) in chromosome seqment 4q12", Genomics 22: 431–436, Jul. 15, 1994.

Aiello, M.D. et al., "Vascular Endothelial Growth Factor in Ocular Fluid of Patients with Diabetic Retinopathy and other Retinal Disorders", The New England Journal of Medicine, 331: pp. 1480–1487, Dec. 1994.

Berkman et al., "Expression of the Vascular Permeability Factor/Vascular Endothelial Growth Factor Gene in Central Nervous System Neoplasms", The Journal of Clinical Investigation, Inc., 91: pp. 153–159, Jan. 1993.

Breier et al., "Expression of vascular endothelial growth factor during embryonic angiogensis & endothelial cell differentiation", Development 114: pp. 521–532, 1992.

Collins et al., Structure and Chromosomal Location of the Gene for Endothelial–Leukocyte Adhesion Molecule1*, The Journal of Biological Chemistry, 266: pp. 2466–2473, 1991.

Connolly et al., "Tumor Vascular Permeability Factor Stimulates Endothelial Cell Growth and Angiogenesis", J. Clin. Invest., 84: pp. 1470–1478, Nov. 1989.

de Vries et al., "The fms–Like Tyrosine Kinase, a Receptor for Vascular Endothelial Growth Factor", Science, 225: pp. 989–991, 1992.

Iademarco et al., "Characterization of the Promoter for Vascular Cell Adhesion Molecule–1 (VCAM–1)", J. Biol. Chem., 2667: pp. 16323–16329, Aug. 1992.

Jahroudi et al., "Endothelial–Cell–Specific Regulation of von Willebrand Factor Gene Expression", Mol. Cell. Biol., 14: pp. 999–1008, Feb. 1994.

Jakeman, et al., "Binding Sites for Vascular Endothelial Growth Factor Are Localized on Endothelial Cells in Adult Rat Tissues", J. Clin. Invest. 89: pp. 244–253, Jan. 1992.

Jakeman et al., "Developmental Expression of Binding Sites and Messenger Ribonucleic Acid for Vascular . . . ", Endocrinology, 133: pp. 848–859, 1993.

Klagsbrun et al., "VEGF/VPF: the angiogensis factor found?", Current Biology, 3: pp. 699–702, 1993.

Lee et al., "Functional Analysis of the Endothelin–1 Gene Promoter", J. biol. Chem., 265: pp. 10446–10450, 1990.

Lenardo et al., "NF–KB: A Pleiotropic Mediator of Inducible and Tissue–Specific Gene Control", Cell, 58: pp. 227–229, 1989.

Leung et al., "Vascular Endothelial Growth Factor Is A Secreted Aniogenic Mitogen", Science, 246: 1306–1390, 1989.

Mathews et al., "A receptor tyrosine kinase cDNA isolated from a population of enriched promitive . . . ", Proc. Natl. Acad. Sci. USA, 33: pp. 9026–9030, Oct. 1991.

Millauer et al., "High Affinity VEGF Binding and Developmental Expression Suggest Flk–1 as a Major . . . ", Cell, 72: pp. 835–846, Mar. 1993.

Moll et al., "Regulation of the Tissue Factor Promoter in Endothelial Cells", J. Biol. Chem., 270: pp. 3849–3857 Feb. 1995.

Orkin, "GATA–Binding Transcription Factors in Hematopoietic Cells", Blood, 80: pp. 575–581, Mar. 1992.

Peters et al, "Vascular endothelial growth factor receptor expression during embryogensis and tissue . . . ", Proc. Natl. Acad. Sci. USA, 90: pp. 9026–9030, Oct. 1993.

Quinn et al., "Fetal liver kinase 1 is a receptor for vascular endothelial growth factor and is selectively expressed in vascular endothelium", Proc. Natl. Acad. Sci. USA, 90: pp. 7533–7537, Aug. 1993.

Ross et al., "The pathogenesis of atherosclerosis: a perspective for the 1990's", Nature, 362: pp. 801–809, Apr. 1993.

Shweiki et al., "Vascular endothelial growth factor induced by hypoxia may mediate hypoxia–initiated angiogensis", Nature, 359: pp. 843–845, Oct. 1992.

Terman et al., "Identification of a new endothelial cell growth factor receptor tyrosine kinase", Onocogene, 6: pp. 1677–1683, 1991.

Terman et al., "Identification of the KDR Tyrosine Kinase as a Receptor for Vascular Endothelial Cell Growth Factor", 187: pp. 1579–1586, Sep. 1992.

Yamaguchi et al., "flk–1, and flt–related receptor tyrosine kinase is an early marker for endothelial cell precursors", Development, 118: pp. 489–498, 1993.

*Primary Examiner*—Jasemine C. Chambers
*Assistant Examiner*—Scott D. Priebe
*Attorney, Agent, or Firm*—Fish & Richardson P.C.

[57] ABSTRACT

A substantially pure DNA comprising an endothelial cell-specific promoter sequence capable of directing endothelial cell-specific transcription of a polypeptide-encoding sequence or an antisense template to which it is operably linked.

10 Claims, 9 Drawing Sheets

```
-15.5kb                              GATA
   -780 CCTCCTTCCC CTGGGCCTAA GGATATCTTG GCTGGAAGCT CTGCTCTGAA AAGGGGCATG GCCAAACTTT CACTAGGGCT CTTCGTTGGG GAGCACGATG
                                                                                                          E Box
   -680 GACAAAAGCC TTCTTGGGGC TAGGCAGGTC ACTTCAAACT TGGAGCCGCC AAATATTTTG GGAAATAGCG GGAATGCTGG CGAACTGGGC AAGTGCGTTT
                                                                                                    Ker
   -580 TCTGATTAAG AGCAACCAGA TTCAGCTTTT TAAACTACAA TTATACTACG TCCCTTGTGG CAAACAAAAT ACCCTTATAC AAAAACCAAA ACTACTGGCA GGAGTCGCTG
   -480 CCAGCTTGCG ACCCGGCATA CTTGGCTGAG TATCCGCTTC TCCCTTGTGG CTCCAAACTG CTGCAGATTC TCGGCCACTT CAGACGCGCG CGATGGCGAA
   -380 GAGGGTCCTG CACTTTGACG CGCCTGGTGA GGGAGCGGTG CTCTTCGCAG CGCTCCTGGT GATGCTCCCC AAATTTCGGG GACCGGCAAG CGATTAAATC
   -280 TTGGAGTTGC TCAGCGCCCG TTACCGAGTA CTTTTTATTT ACACCAGAAA CAAAGTTGTT GCTCTCTCCT GGGGCGACTTG GGGCCCAGCG
                E Box                                         AP2          NFκB/Sp1    Sp1    AP2
   -180 CAGTCCAGTT GTGTGGGGAA ATGGGGAGAT GTAAATGGGC TTGGGGAGCT GGAGATCCCC CGGGTGAGGG GCGGGCTGG CCGCACGGGA
        NFκB                   AP2/Sp1                Sp1
    -80 GAGCCCCTCC TCCGCCCCGG CCCCGCCCCG CATGGCCCCG CCTCCCGCCT CTAGAGTTTC GGCTCCAGCT ACTGAGTCCC GGGACCCCGG
                                                                                                  GATA
    +21 GAGAGCGGTC AGTGTGTGGT CGCTGCGTTT CCTCTGCCTG CGCCGGGCAT CCGCAGAAAG TCCGTCTGGC AGCCTGGATA TCCTCTCCTA
                                                                           E Box
   +121 CCGGCACCCG CAGACGCCCC TGCAGCCGCC CGGGCTCCCT GGTCGGCGCC GAGAAAGAAC CGGCTCCCGA GCTCAACTGT AGCCCTGTGC GGGGTGCCGC GAGTTCCACC
   +221 TCCGCGCCTC CTTCTCTAGA CAGGCGCTGG GAGAAAGAAC CGGCTCCCGA GTTCTGGGCA TTTCGCCCGG gtaaggagcc CTCGAGGTGC AGGATGCAGA GCAAGGTGCT
                                                                                                           M  Q   S  K  V  L
   +321 GCTGGCCGTC GCCCTGTGGC TCTGCGTGGA GACCCGGGCC GCCTCTGTGG gtaaggagcc cactctggag gaggaaggca gacaggtcgg gtgagggcgg
         L  A  V   A  L  W   L  C  V  E   T  R  A    A  S  V (SEQ ID NO: 15)
   +421 agaggacctg aaagccagat ctaactcgga atcgtagagc tggagagttg gacaggactt gacattt (SEQ ID NO: 7)
```

FIG. 1A

FIG. 2B
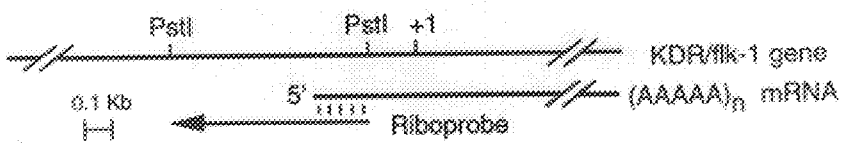
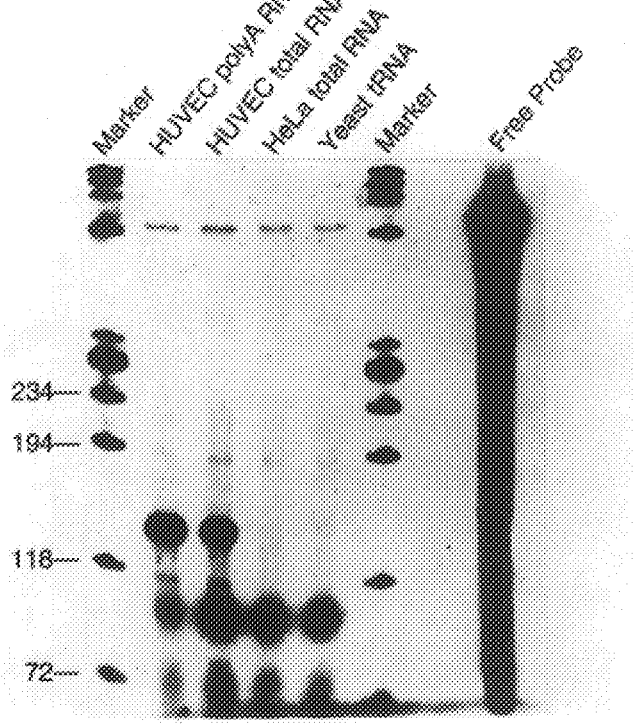
FIG. 2C

ENDOTHELIAL-CELL SPECIFIC PROMOTER

BACKGROUND OF THE INVENTION

The field of the invention is endothelial cell-specific gene transcription.

Vascular endothelial growth factor (VEGF) is a potent and specific endothelial cell mitogen (Connolly et al., 1989, J. Clin. Invest. 84:1470–1478; Leung et al., 1989, Science 246:1306–1309). Through interactions with its receptors, Kinase-insert Domain-containing Receptor/fetal liver kinase-1 (KDR/flk-1) and flt1, VEGF has critical roles in growth and maintenance of vascular endothelial cells and in the development of new blood vessels in physiologic and pathologic states (Aiello et al., 1994, New Engl. J. Med. 331:1480–1487; Shweiki et al., 1992, Nature 359:843–845; Berkman et al., 1993, J. Clin. Invest. 91:153–159). The patterns of embryonic expression of VEGF suggest that it is crucial for differentiation of endothelial cells from hemangioblasts and for development of blood vessels at all stages of growth (Jakeman et al., 1993, Endocrinology 133:848–859; Breier et al., 1992, Development 114:521–532). Among many potentially angiogenic factors, VEGF is the only one whose pattern of expression, secretion, and activity suggests a specific angiogenic function in normal development (Klagsbrun et al., 1993, Current Biology 3:699–702).

High-affinity receptors for VEGF are found only on endothelial cells, and VEGF binding has been demonstrated on macro- and microvascular endothelial cells and in quiescent and proliferating endothelial cells (Jakeman et al., 1993, Endocrinology 133:848–859; Jakeman et al., 1992, Clin. Invest. 89:244–253). The tyrosine kinases, KDR/flk-1 and flt1, have been identified as candidate VEGF receptors by affinity cross-linking and competition-binding assays (de Vries et al., 1992, Science 255:989–991; Millauer et al., 1993, Cell 72:835–846; Terman et al., 1992, Biochem. Biophys. Res. Commun. 187:1579–1586). These two receptor tyrosine kinases contain seven similar extracellular immunoglobulin domains and a conserved intracellular tyrosine kinase domain interrupted by a kinase insert (de Vries et al., 1992, Science 255:989–991; Matthews et al., 1991, Proc. Natl. Acad. Sci. U.S.A 88:9026–9030; Terman et al., 1001, Oncogene 6:1677–1683); they are expressed specifically by endothelial cells in vivo (Millauer et al., 1993, Cell 72:835–846; Peters et al., 1993, Proc. Natl. Acad. Sci. U. S. A. 90:8915–8919; Quinn et al., 1993, Proc. Natl. Acad. Sci. U.S.A. 90:7533–7537; Yamaguchi et al., 1993, Development 118:489498). In situ hybridization in the developing mouse has demonstrated that KDR/flk-1 is expressed in endothelial cells at all stages of development, as well as in the blood islands in which endothelial cell precursors first appear (Millauer et al., 1993, Cell 72:835–846. KDR/flk-1 is a marker for endothelial cell precursors at their earliest stages of development (Yamaguchi et al., 1993, Development 118:489–498).

The vascular endothelium is critical for physiologic responses including thrombosis and thrombolysis, lymphocyte and macrophage homing, modulation of the immune response, and regulation of vascular tone. The endothelium is also intimately involved in the pathogenesis of vascular diseases such as atherosclerosis (Ross, R., 1993, Nature 362:801–809). Although a number of genes expressed in the endothelium have been characterized (Collins et al., 1991, J. Biol. Chem. 266:2466–2473; Iademarco et al., 1992, J. Biol. Chem. 267:16323–16329; Jahroudi et al., 1994, Mol. Cell. Biol. 14:999–1008; Lee et al., 1990, J. Biol. Chem. 265:10446–10450), expression of these genes is either not limited to vascular endothelium (e.g., the genes encoding von Willebrand factor, endothelin-1, vascular cell adhesion molecule-1) or is restricted to specific subpopulations of endothelial cells (e.g., the gene for endothelial-leukocyte adhesion molecule-1).

SUMMARY OF THE INVENTION

The invention features a substantially pure DNA, i.e., a promoter sequence, which regulates endothelial cell-specific transcription of a polypeptide-encoding sequence to which it is operably linked. The DNA of the invention contains a sequence substantially identical to nucleotides −225 to −164 of the KDR/flk-1 promoter, i.e., 5' TTGTTGCTCTGGGAT-GTTCTCTCCTGGGCGACTTGGGGC-CCAGCGCAGTCCAGTTGT GTGGG 3' (SEQ ID NO:1). By "substantially identical" is meant at least 80% identical to a reference DNA sequence; that is, up to 20% of the basepairs of the reference DNA sequence can be replaced with an alternative basepair (e.g., G-C replaced with A-T, T-A, or C-G), provided that the transcription-promoting activity of the altered sequence is the same or greater than that of the reference sequence. The DNA may also include a sequence substantially identical to nucleotides −95 to −77 of the KDR/flk-1 promoter, i.e., 5' GCTGGCCGCACGG-GAGAGC 3' (SEQ ID NO:2), a sequence substantially identical to nucleotides −95 to −60 of the KDR/flk-1 promoter, i.e., 5' GCTGGCCGCACGGGAGAGCCCCTC-CTCCGCCCCGGC 3' (SEQ ID NO:3), a sequence substantially identical to nucleotides +105 to +127 of the KDR/flk-1 promoter, i.e., 5' GGATATCCTCTCCTACCGGCAC 3' (SEQ ID NO:4, or a combination thereof. Preferably, the 5' to 3' orientation of sequences is SEQ ID NO:1; SEQ ID NO:2 or SEQ ID NO:3; and SEQ ID NO:4. However, any orientation of these sequences which promotes endothelial cell-specific transcription is within the invention. The DNA may include a nonspecific sequence between any two of the defined sequences, and/or at either or both ends. Preferably, this nonspecific (i.e., sequence other than SEQ ID NO:1–4 will constitute no more than 80% of the entire promoter sequence. Most preferably, it is substantially identical to the sequence shown in Table 1 (SEQ ID NO:5) or Table 2 (SEQ ID NO:6)

A "substantially pure DNA" as used herein refers to a DNA which has been purified from the sequences which flank it in a naturally occurring state, i.e., a DNA fragment which has been removed from the sequences which are normally adjacent to the fragment, e.g., the sequences adjacent to the fragment in the genome in which it naturally occurs.

A substantially pure DNA containing a sequence substantially identical to nucleotides −225 to +268 of the KDR/flk-1 promoter (SEQ ID NO:5; Table 1) or nucleotides −225 to +127 of the KDR/flk-1 promoter (SEQ ID NO:6; Table 2) and which regulates endothelial cell-specific transcription of a polypeptide-encoding sequence or antisense template to which it is operably linked is also within the invention.

TABLE 1

−225 to +268

TTGTTGCTCTGGGATGTTCTCTCCTGGGCGACTTGGGGCCCAGCGCAGTCCAGTTGTGTG

GGGAAATGGGGAGATGTAAATGGGCTTGGGGAGCTGGAGATCCCCGCCGGGTACCCGGGT

GAGGGGCGGGGCTGGCCGCACGGGAGAGCCCCTCCTCCGCCCCGGCCCCGCCCCGCATGG

CCCCGCCTCCGCGCTCTAGAGTTTCGGCTCCAGCTCCCACCCTGCACTGAGTCCCGGGAC

CCCGGGAGAGCGGTCAGTGTGTGGTCGCTGCGTTTCCTCTGCCTGCGCCGGGCATCACTT

GCGCGCCGCAGAAAGTCCGTCTGGCAGCCTGGATATCCTCTCCTACCGGCACCCGCAGAC

GCCCCTGCAGCCGCCGGTCGGCGCCCGGGCTCCCTAGCCCTGTGCGCTCAACTGTCCTGC

GCTGCGGGGTGCCGCGAGTTCCACCTCCGCGCCTCCTTCTCTAGACAGGCGCTGGGAGAA

AGAACCGGCTCCC   (SEQ ID NO:5)

TABLE 2

−225 to +127

TTGTTGCTCTGGGATGTTCTCTCCTGGGCGACTTGGGGCCCAGCGCAGTCCAGTTGTGTG

GGGAAATGGGGAGATGTAAATGGGCTTGGGGAGCTGGAGATCCCCGCCGGGTACCCGGGT

GAGGGGCGGGGCTGGCCGCACGGGAGAGCCCCTCCTCCGCCCCGGCCCCGCCCCGCATGG

CCCCGCCTCCGCGCTCTAGAGTTTCGGCTCCAGCTCCCACCCTGCACTGAGTCCCGGGAC

CCCGGGAGAGCGGTCAGTGTGTGGTCGCTGCGTTTCCTCTGCCTGCGCCGGGCATCACTT

GCGCGCCGCAGAAAGTCCGTCTGGCAGCCTGGATATCCTCTCCTACCGGCAC   (SEQ ID NO:6)

The DNA of the invention may be operably linked to and functions to regulate endothelial cell-specific transcription of a sequence encoding a polypeptide that is not KDR/flk-1. Examples of such polypeptides include tissue plasminogen activator (tPA), p21 cell cycle inhibitor, and nitric oxide synthase. By "operably linked" is meant able to promote transcription of an mRNA corresponding to a polypeptide-encoding or antisense template located downstream on the same DNA strand.

The invention also includes a vector containing the DNA of the invention, a method of directing endothelial cell-specific expression of a polypeptide by introducing the vector into an endothelial cell, and an endothelial cell containing the vector.

The vector of the invention can be used for gene therapy, such as a method of inhibiting arteriosclerosis in an animal involving contacting an artery of the animal with the vector of the invention which directs the production of a polypeptide capable of reducing or preventing the development of arteriosclerosis, e.g., a polypeptide which reduces proliferation of smooth muscle cells, e.g., interferon-γ or atrial natriuretic polypeptide.

The invention also includes compositions and methods of carrying out antisense therapy. For example, the invention includes a substantially pure DNA with a sequence substantially identical to SEQ ID NO:1 which regulates endothelial cell-specific transcription of an antisense template to which it is operably linked, e.g., an antisense template the transcription product of which prevents translation of mRNA into an endothelial cell polypeptide. By the term "antisense template" is meant a DNA which is transcribed into an RNA which hybridizes to mRNA. Preferably, the endothelial cell polypeptide is KDR/flk-1. For example, the antisense RNA transcript which binds to and thereby prevents or reduces translation of an mRNA encoding KDR/flk-1, a protein involved in angiogenesis, can be used to treat cancer by contacting a tumor site in an animal with the DNA of the invention to reduce or prevent angiogenesis at the tumor site.

Translation of other endothelial cell polypeptides may also be reduced or prevented in this manner. For example, cell cycle proteins, coagulation factors, e.g., von Willebrand factor, and endothelial cell adhesion factors, e.g., intercellular adhesion molecule (ICAM-1) or vascular cell adhesion molecule (VCAM-1).

Other features and advantages of the invention will be apparent from the following description of the preferred embodiments thereof, and from the claims.

DETAILED DESCRIPTION

The drawings will first be described.

FIG. 1A is a diagram of the human KDR/flk-1 promoter. Restriction enzyme sites are indicated above the nucleotide sequence, and nucleotide sequences −780 to +487 (SEQ ID NO:7) are numbered on the left of the nucleotide sequence. The transcription start site is indicated by a curved arrow. Potential cis-acting elements are underlined. PstI sites which were used to generate the riboprobe are double underlined, and the oligonucleotide which was used for primer extension are underlined with an arrow.

FIG. 1B is a diagram of the murine KDR/flk-1 promoter. Restriction enzyme sites are indicated above the nucleotide sequence. Nucleotide sequences −295 to +205 (SEQ ID NO:8) are numbered and potential cis-acting elements are indicated as in FIG. 1A. An asterisk indicates the 5' end of the cDNA.

FIG. 2A is a photograph of an electrophoretic gel showing the results of a primer extension analysis of the KDR/flk-1 transcription start site. The oligonucleotide underlined with an arrow in FIG. 1A was hybridized to 20 μg of total RNA from human umbilical vein endothelial cells (HUVEC) and HeLa cells or 3 μg of polyA+ HUVEC RNA and yeast tRNA. Extension products were analyzed on an 8% polyacrylamide gel (lanes 1–4: Yeast tRNA; HeLa total RNA; HUVEC total RNA; HUVEC polyA+ RNA). A Sanger sequencing reaction primed on a plasmid DNA template (with the same oligonucleotide primer) was run next to the primer extension analyses (lanes 5–8: G; A; T; C).

FIG. 2B is a diagram showing the strategy for mapping the transcription start site of the KDR/flk-1 gene by ribonuclease protection.

FIG. 2C is a photograph of an electrophoretic gel showing a ribonuclease protection analysis of the KDR/flk-1 transcription start site. Total RNA from HUVEC and HeLa cells or polyA+ HUVEC RNA and yeast tRNA were incubated with a 559-bp $^{32}$P-labeled riboprobe spanning the immediate 5' region of the human KDR/flk-1 gene. The annealing products were digested with RNase. Protected fragments were analyzed on a 4% polyacrylamide gel. The size markers (bp) were prepared by radiolabeling ΦX174 RF DNA digested with HaeIII.

Figure 5:
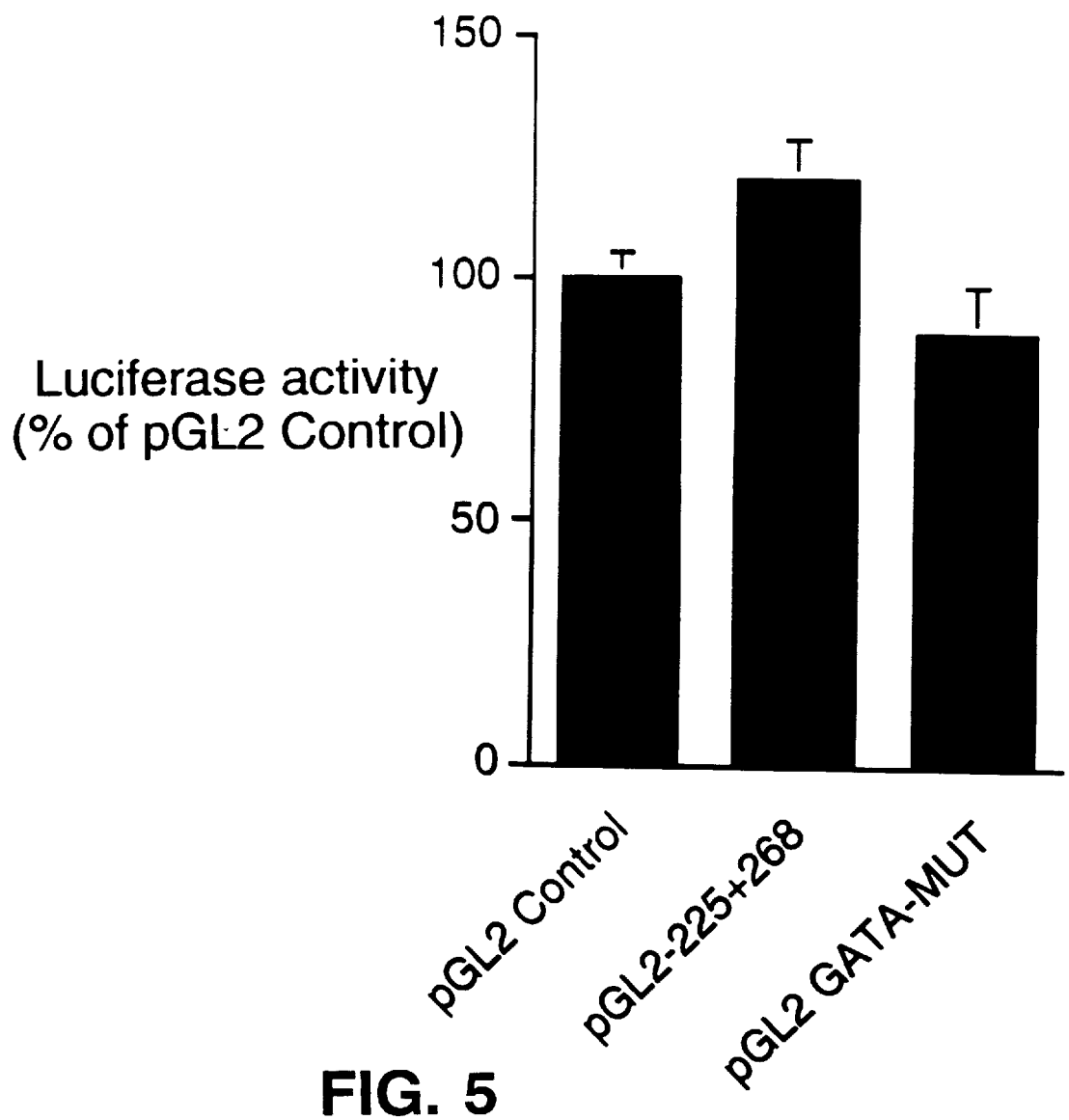

FIG. 5 is a bar graph showing the effect of a GATA site mutation on KDR/flk-1 promoter activity. Mutation of the GATA site at position +107 does not decrease the ability of the KDR/flk-1 promoter to direct transcription. When transfected into BAEC, the plasmid pGL2-225+268 directed luciferase expression comparable to that directed by pGL2 Control, which contains the SV40 promoter and enhancer. When three bp of the GATA motif at +107 were mutated to create pGL2 GATA-MUT, there was no significant difference in promoter activity.

Figure 6A:
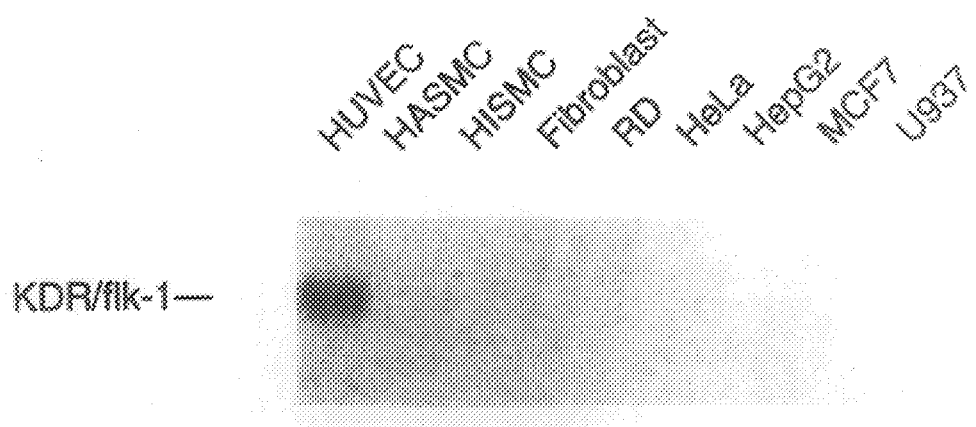

FIG. 6A is a photograph of a Northern blot analysis showing that KDR/flk-1 RNA expression is restricted to endothelial cells in culture. RNA was extracted from cells in culture and analyzed by Northern blotting using a human KDR/flk-1 cDNA probe. The following cell types were tested: HUVEC, human umbilical vein endothelial cells; HASMC, human aortic smooth muscle cells; HISMC, human intestinal smooth muscle cells; Fibroblast, human cultured fibroblasts; RD, human embryonal rhabdomyosarcoma cells; HeLa, human epidermoid carcinoma; HepG2, human hepatoma cells; MCF7, human breast adenocarcinoma cells; and U937, human histiocytic lymphoma cells.

Figure 6B:
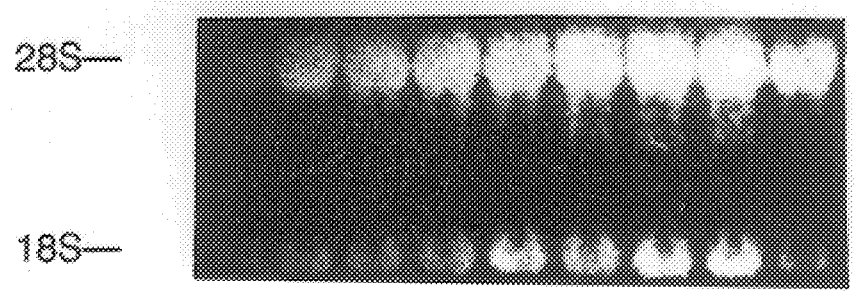

FIG. 6B is a photograph of the same agarose gel shown in FIG. 6A which was stained with ethidium bromide (to visualize ribosomal RNA) to show the amount of RNA loaded in each lane.

Figure 7:
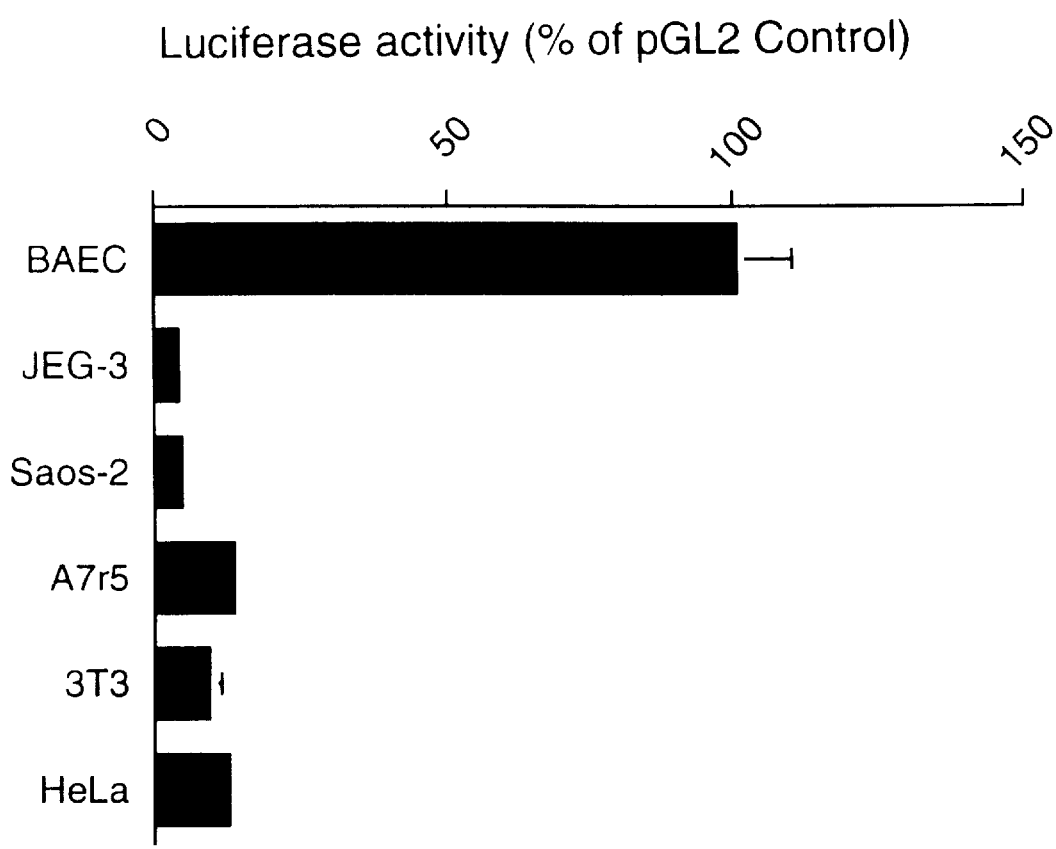

FIG. 7 is a bar graph showing the results of a luciferase assay. High-level activity of the KDR/flk-1 promoter was found to be specific to endothelial cells. The luciferase reporter construct pGL2-4kb+296 was transfected into cells in culture, and transfection efficiency was assessed by monitoring cotransfection with pSVβgal. Results are corrected for transfection efficiency and expressed as a percentage of pGL2 Control activity for each cell type. The following cell types were tested: BAEC, bovine aortic endothelial cells; JEG-3, human choriocarcinoma cells; Saos-2, human osteosarcoma cells; A7r5, rat fetal smooth muscle cells; 3T3, mouse fibroblasts; and HeLa, human epidermoid carcinoma cells.

Screening of Human and Mouse Genomic Libraries

A 567-bp human KDR/flk-1 cDNA fragment was generated from HUVEC total RNA by reverse-transcriptase polymerase chain reaction (RT-PCR). This fragment was radiolabeled with [α-$^{32}$P]dCTP and used to screen a phage library of human placenta genomic DNA in the vector λFixII (Stratagene, La Jolla, Calif.). Likewise, a 451-bp mouse KDR/flk-1 cDNA was generated by RT-PCR from mouse lung total RNA and used to screen a phage library of mouse placenta genomic DNA in the vector λDashII (Stratagene). Hybridizing clones were isolated and purified from each library, and phage DNA was prepared according to standard procedures.

Cell Culture and mRNA Isolation

BAEC were isolated and cultured in Dulbecco's modified Eagle's medium (JRH Biosciences, Lenexa, Kans.) supplemented with 10% fetal calf serum (HyClone, Logan, Utah), 600 μg of glutamine/ml, 100 units of penicillin/ml, and 100 μg of streptomycin/ml. Cells were passaged every 3–5 days and cells from passages 4–8 were used for transfection experiments. Saos-2 human osteosarcoma cells (ATCC HTB-85), HeLa human epidermoid carcinoma cells (ATCC CRL-7923), HepG2 human hepatoma cells (ATCC HB-8065), human fibroblasts (ATCC CRL-1634), U937 human histiocytic lymphoma cells (ATCC CRL-7939), RD human embryonal rhabdomyosarcoma cells (ATCC CCL-136), MCF7 human breast adenocarcinoma cells (ATCC HTB-22), JEG-3 human choriocarcinoma cells (ATCC HTB-36), A7r5 fetal rat aortic smooth muscle cells (ATCC CRL-1444), and NIH 3T3 mouse fibroblasts (ATCC CRL-1658) were obtained from the American Type Culture Collection. Primary-culture HUVEC were obtained from Clonetics Corp. (San Diego, Calif.) and were grown in EGM medium containing 2% fetal calf serum (Clonetics). Primary-culture human aortic and intestinal smooth muscle cells were also obtained from Clonetics Corp. All cells were cultured in conditions identical to those for BAEC, with the exception that medium used for smooth muscle cells was supplemented with 25 mm HEPES (Sigma, St. Louis, Mo.) and that HUVEC were cultured in EGM medium containing 2% fetal calf serum. Primary-culture cells were passaged every 4–6 days, and cells from passages 3–5 were analyzed. Total RNA from cells in culture was prepared by guanidinium isothiocyanate extraction and centrifugation through cesium chloride.

DNA Sequencing

Restriction fragments derived from the human and mouse KDR/flk-1 genomic phage clones were subcloned using standard techniques into pSP72 (Promega, Madison, Wis.) or pBluescript II SK (Stratagene) and sequenced from alkaline-denatured double-stranded plasmid templates by the dideoxy chain termination method with SEQUENASE® 2.0 DNA polymerase (United States Biochemical, Cleveland, Ohio). DNA was sequenced from both directions at least twice, and both dGTP and dITP sequencing protocols were used to resolve compression artifacts in the highly GC-rich 5' flanking region of the human and mouse KDR/flk-1 genes. Sequence analysis was performed with the GCG software package (Genetics Computer Group, Madison, Wis.).

Primer Extension Analysis

Primer extension analysis was performed according to known methods, e.g., the method of Fen et al., 1993, Biochemistry 32:7932–7938. A synthetic oligonucleotide primer (5' CTGTCTAGAGAAGGAGGCGCGGAGGTG-GAACT 3'; SEQ ID NO:9) complementary to the 5' end of the human KDR/flk-1 cDNA (FIG. 1A) was end-labeled with [$\gamma$-$^{32}$P]ATP and hybridized to 20 µg of each RNA sample, which was then subjected to reverse transcription. Extension products were analyzed by electrophoresis on an 8% denaturing polyacrylamide gel.

Ribonuclease Protection Assay

A 559-bp PstI—PstI fragment of the human KDR/flk-1 gene (FIG. 2B) was cloned in pSP72 as the template for in vitro transcription of an $\alpha$-$^{32}$P-labeled antisense RNA with T7 RNA polymerase (Boehringer Mannheim, Indianapolis, Ind.). Gel-purified riboprobe (5×10$^5$ cpm) was hybridized with 20 µg of total RNA or 3 µg of polyA RNA plus 17 µg of yeast tRNA at 55° C. for 16 h in an annealing buffer containing 20 mm Tris-HCl, pH 7.40, 400 mm NaCl, 1 mm EDTA, and 0.1% sodium dodecyl sulfate in 75% formamide. After the RNA had been annealed, the unhybridized RNA was digested for 45 min at room temperature with 200 U RNAse T1 (Boehringer Mannheim) and 0.3 U RNAse A (Boehringer Mannheim) in a buffer containing 10 mm Tris-HCl, pH 7.50, 300 mm NaCl, 5 mm EDTA. The digestion products were then treated with proteinase K, extracted with phenol:chloroform, and analyzed by electrophoresis on a 4% denaturing polyacrylamide gel.

Northern Analysis

Total RNA (10 µg) from cells in culture was fractionated on a 1.3% formaldehyde-agarose gel and transferred to a nitrocellulose filter. The human KDR/flk-1 cDNA probe was labeled with $^{32}$p by random priming, the labeled probe was then used to hybridize the filter. The filter was then autoradiographed for 16 h on Kodak XAR film at −80° C.

Plasmids

Plasmids pGL2 Basic and pGL2 Control contained the firefly luciferase gene (Promega). pGL2 Basic had no promoter, whereas pGL2 Control was driven by the SV40 promoter and enhancer. The plasmid pSV$\beta$GAL (Promega) contained the $\beta$-galactosidase gene driven by the SV40 promoter and enhancer.

Reporter constructs containing fragments of the human KDR/flk-1 5' flanking region were inserted into pGL2 Basic and named according to the length of the fragment (from the transcription start site) in the 5' and 3' directions. For example, plasmid pGL2-4kb+296 contained a human KDR/flk-1 promoter fragment extending from approximately −4 kb 5' of the transcription start site to position +296 inserted into pGL2 Basic. Plasmids pGL2-4kb+296 and pGL2-900+296 were created by restriction digestion of purified phage DNA by using 5' BamHI and PvuII sites, respectively, and the 3' XhoI site at position +296. Plasmids pGL2-716+268, pGL2-570+268, pGL2-323+268, pGL2-225+268, pGL2-164+268, pGL2-37+268, pGL2-225+127, pGL2-225+105, pGL2-225+56, and pGL2-225+5 were created from promoter fragments generated by PCR of human KDR/flk-1 phage DNA. Plasmids pGL2-116+268, pGL2-95+268, pGL2-77+268, pGL2-60+268, and pGL2-12+268 were created by digesting the promoter fragment contained in plasmid pGL2-164+268 from the 5' end with exonuclease III (Pharmacia Biotech, Piscataway, N.J.). Plasmid pGL2 GATA-MUT was identical to pGL2-225+268 except that bp +108 to +110 were mutated in the plasmid pGL2 GATA-MUT. All constructs were sequenced from the 5' and 3' ends to confirm orientation and sequence.

Mutagenesis

Site-directed mutagenesis of the atypical GATA sequence located in the first exon of the human KDR/flk-1 5' flanking region was performed by PCR using to the method of Higushi et al., 1988, Nucleic Acids Res. 16:7351–7367. A DNA fragment containing human KDR/flk-1 bp −225 to +268 was used as a template. The sequence TGGATATC was mutated to TGGTCGTC by using one set of mismatched primers, 5' TCTGGCAGCCTGGTCGTCCTCTC-CTA 3' (SEQ ID NO:10) and 5'TAGGAGAGGACGAC-CAGGCTGCCAGA 3' (SEQ ID NO:11), and one set of primers flanking both ends of the template, 5' TGCCTC-GAGTTGTTGCTCTGGGATGTT 3' (SEQ ID NO:12) and 5' TGTAAGCTTGGGAGCCGGTTCTTTCTC 3' (SEQ ID NO:13). The sequence of the mutated PCR fragment was confirmed by the dideoxy chain termination method.

Transfections

All cell types were transfected by the calcium phosphate method known in the art with the exception of A7r5 cells, which were transfected with DOTAP (Boehringer Mannheim) as instructed by the manufacturer. In all cases, 20 µg of the appropriate reporter construct was transfected along with 2.5 µg of pSV$\beta$gal to correct for variability in transfection efficiency. Cell extracts were prepared 48 h after transfection by a detergent lysis method (Promega). Luciferase activity was measured in duplicate for all samples with an EG&G Autolumat 953 luminometer (Gaithersberg, Md.) and the Promega Luciferase Assay system. $\beta$-Galactosidase activity was assayed using known methods, e.g., Lee et al., 1990, J. Biol. Chem. 265:10446–10450.

The ratio of luciferase activity to $\beta$-galactosidase activity in each sample served as a measure of the normalized luciferase activity. The normalized luciferase activity was divided by the activity of pGL2 Control and expressed as relative luciferase activity. Each construct was transfected at least six times, and data for each construct are presented as the mean ±SEM. Relative luciferase activity among constructs was compared by a factorial analysis of variance followed by Fisher's least significant difference test. Statistical significance was accepted at $p<0.05$.

Isolation and Characterization of Human and Murine KDR/flk-1 Genomic Clones

Figure 1B:
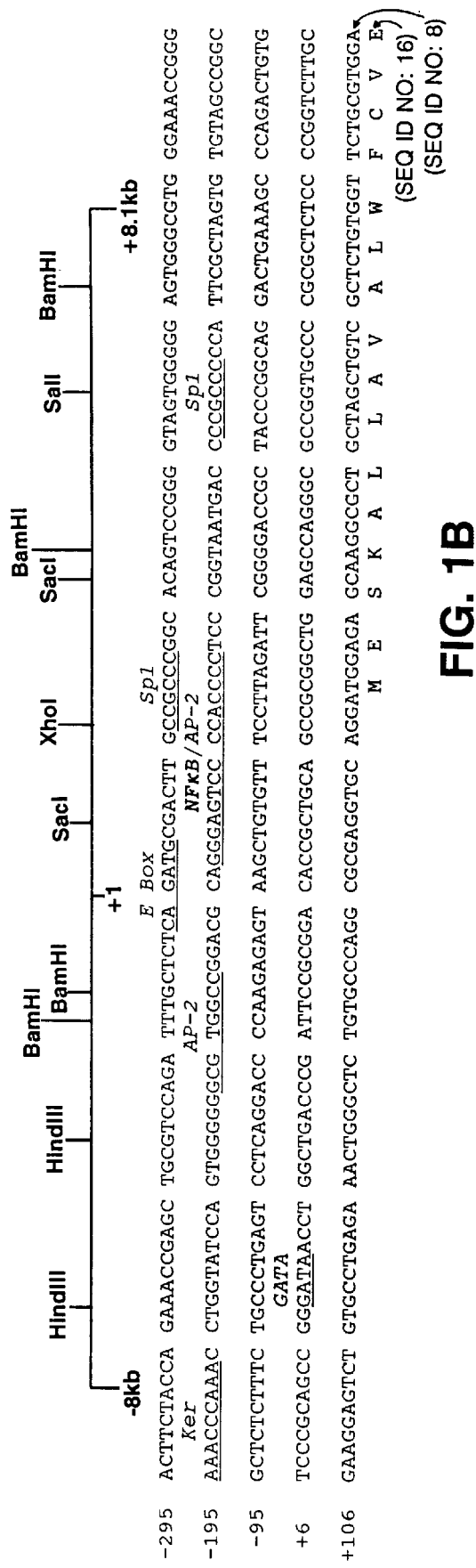

Initial screening of a human placental phage library with a human KDR/flk-1 cDNA probe yielded a positive clone that was examined by restriction enzyme DNA mapping, subcloning, and sequencing. The 780-bp sequence of the promoter and first exon is shown in FIG. 1A. Likewise, a murine KDR/flk-1 cDNA probe was used to screen a murine placental phage library, and one clone was identified and characterized. The sequence of the mouse KDR/flk-1 promoter is shown in FIG. 1B.

Identification of the Transcription Start Site of Human KDR/flk-1

Figure 2A:
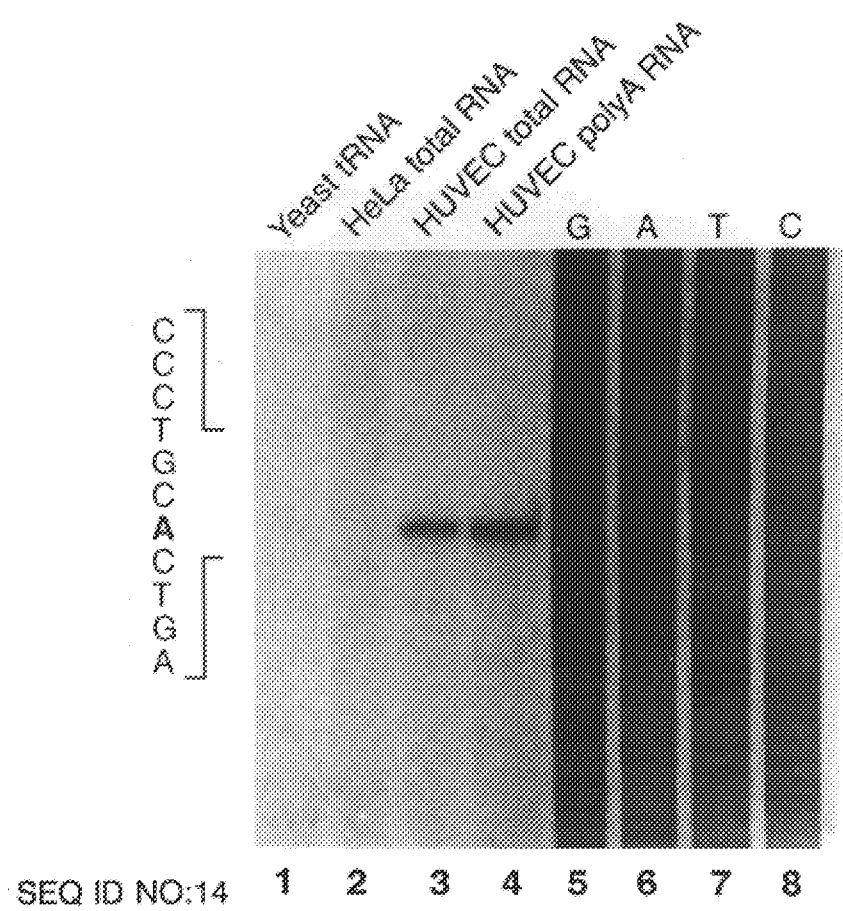

To identify the transcription start site of the human KDR/flk-1 gene, primer extension was performed with a complementary oligonucleotide probe corresponding to bp +212 to +243 (underlined with arrow, FIG. 1A). Primer extension was performed on total RNA from HUVEC and HeLa cells and on polyA RNA from HUVEC. Gene transcription was found to be initiated only in endothelial cells (FIG. 2A). A single transcription start site, corresponding to a nucleotide located 303 bp 5' of the site of translation initiation, i.e., the methionine initiation codon, was identified. This nucleotide was designated +1. The transcription start site is highlighted in bold in the sequence, CCCTG-CACTGA (SEQ ID NO:14) (see FIGS. 1A and 2A). The 5'CA3' nucleotide pair at this position is the most common site for transcription initiation.

To confirm the results of the primer extension studies, a ribonuclease protection analysis was performed using an antisense riboprobe generated from a 559-bp genomic PstI—PstI fragment extending 5' from position +146 (FIG. 2B; the PstI sites are double underlined in FIG. 1A). Incubation of this probe with HUVEC polyA RNA and HUVEC total RNA, but not with total RNA from HeLa cells, resulted in protection of a single fragment corresponding in length to the distance between the 3' PstI site and the transcription start site identified by primer extension (FIG. 2C). Despite the absence of a TATA consensus sequence, transcription of the human KDR/flk-1 gene was found to begin from a single site located 303 bp 5' of the translation initiation codon (FIG. 1A, curved arrow).

Identification of Cis-Acting Sequences

The 5' flanking sequence of the human KDR/flk-1 gene contains regions rich in G and C residues and lacks TATA and CCAAT boxes near the transcription start site (FIG. 1A). Comparison of this 5' flanking sequence with sequences in the Transcription Factors Database revealed a series of five Sp1 sites located between human KDR/flk-1 nucleotides −124 and −39. There are two AP-2 consensus sites at positions −95 and −68 and two inverted NFκB binding elements at −130 and −83 interspersed among the Sp1 sites. Two atypical GATA consensus sequences (both GGATAT) are present in the KDR/flk-1 promoter, one at position −759 and the other at position +107 within the untranslated portion of the first exon. In addition, multiple CANNTG elements are located in the promoter at positions −591, −175, +71, and +184; CANNTG elements can be bound by E-box binding proteins. The sequence AAACCAAA, which is conserved among genes expressed preferentially in keratinocytes, is present at human KDR/flk-1 position −508.

The human and mouse KDR/flk-1 promoters were compared to identify conserved consensus sequences for nuclear proteins (FIG. 1B). Elements conserved between the two species include two Sp1 sites located at positions −244 and −124 relative to the 5' end of the reported mouse cDNA sequence, two AP-2 sites at positions −168 and −148, a noninverted NFκB site at position −153, and the keratinocyte element AAACCAAA at position −195. An atypical GATA element (GGATAA) is located in the untranslated portion of the first exon of the mouse promoter at position +18; an atypical GATA element (GGATAT) is located similarly in the human promoter. Also, a CANNTG sequence is present 12 bp 5' of the G- and C-rich sequences of the promoter at mouse KDR/flk-1 position −257, a location analogous to that of the CANNTG element at position −175 of the human promoter. Conservation of these elements across species suggests that these regulatory elements have functional significance.

Deletion Analysis of the Human KDR/flk-1 Promoter

Figure 3A:
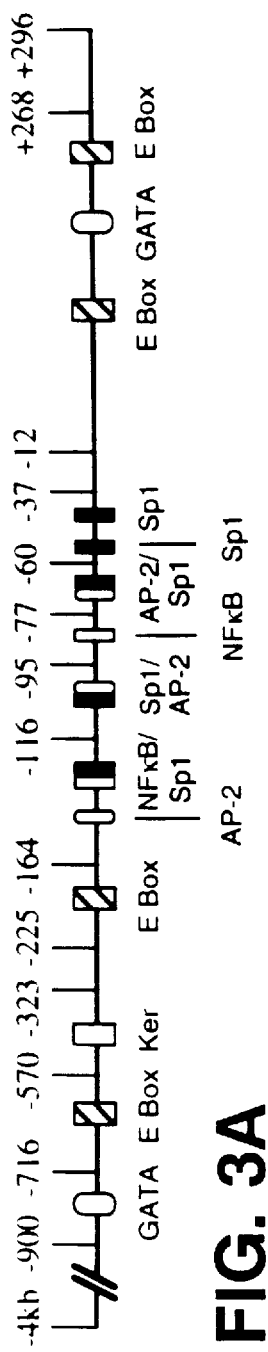
FIG. 3A is a diagram showing the location of 5' deletion sites in the KDR/flk-1 promoter. Location of deletion sites is shown in relation to consensus sequences for known nuclear proteins.
Figure 3B:
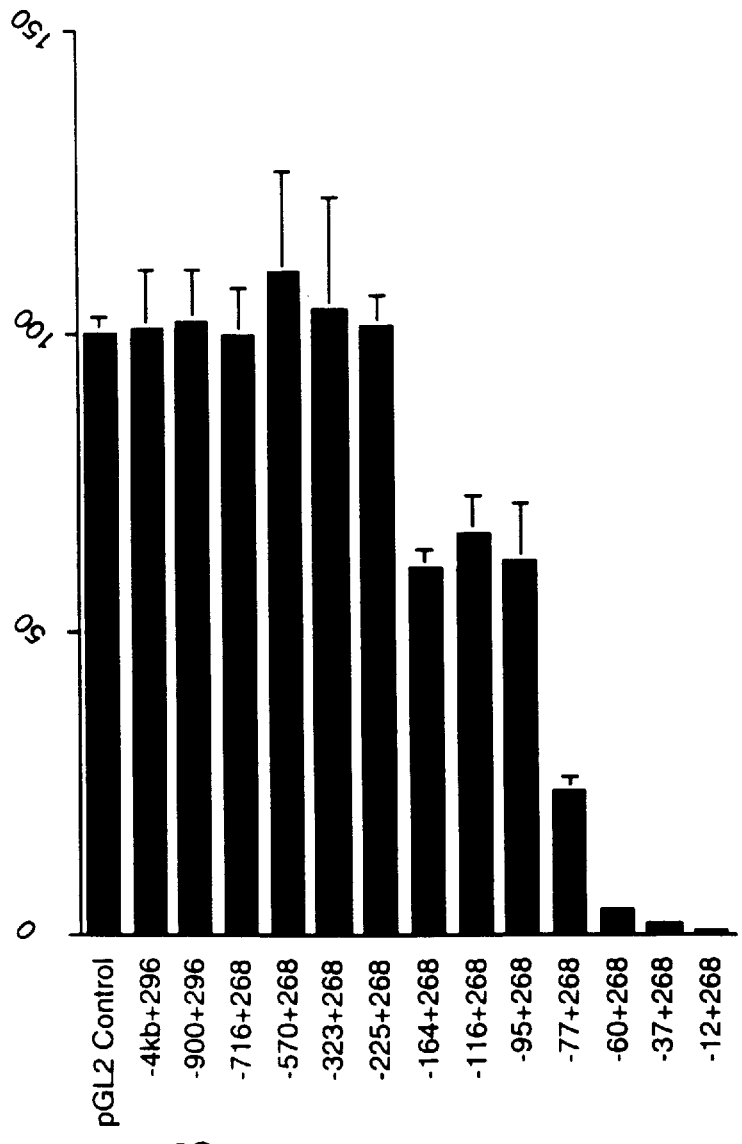
FIG. 3B is a bar graph showing the results of a functional analysis of the human KDR/flk-1 promoter by transfection of luciferase reporter constructs containing serial 5' deletions into bovine aortic endothelial cells (BAEC). All constructs were cotransfected with pSVβgal to correct for transfection efficiency, and luciferase activity was expressed as a percentage of pGL2 Control (mean ±SEM).

To identify DNA elements important for basal expression of KDR/flk-1 in endothelial cells, a series of luciferase reporter plasmids containing serial 5' deletions through the promoter region was constructed (FIGS. 3A and 3B). These plasmid constructs in pGL2 Basic were cotransfected into BAEC with pSVβgal (to correct for differences in transfection efficiency) and the luciferase activity was normalized to that of the pGL2 Control vector driven by the SV40 promoter/enhancer. The activity of the longest human KDR/flk-1 genomic fragment, spanning bp −4kb to +296, was similar to that of the powerful SV40 promoter/enhancer and consistent with the high level of KDR/flk-1 mRNA expression in endothelial cells. Similar levels of activity were produced in constructs containing as much as 15.5 kb of 5' flanking sequence. Serial 5' deletions from bp −4kb to −225 caused no significant change in promoter activity, implying that elements in this region are not important for basal activity of the KDR/flk-1 promoter. Deletion of sequences between bp −225 and −164 significantly reduced KDR/flk-1 promoter activity to 63% of the activity of the full promoter fragment (p<0.05). These data suggest the presence of positive regulatory elements in this region. Deletion of bp from −95 to −77, a sequence that contains one AP-2 site and one NFκB site, resulted in a further significant decrease in activity to 20% that of pGL2-4kb+296 (p<0.05). Further deletion of bp from −77 to −60, an area containing an overlapping AP-2/Sp1 site, significantly reduced KDR/flk-1 promoter activity to less than 5% that of pGL2-4kb+296 (p<0.05). Thus, 5' deletion analysis revealed that many positive regulatory elements in the KDR/flk-1 promoter are necessary for high-level expression of the gene.

The deletion analyses described above indicate that three sequences within the 5' flanking region of the KDR/flk-1 gene contain elements important for expression in endothelial cells. Potential binding sites for Sp1, AP-2, NFκB, and E-box proteins located within these three positive regulatory elements in the human KDR/flk-1 gene are also present in the mouse 5' flanking sequence, thus suggesting that they are functional binding domains. AP-2 is a developmentally regulated trans-acting factor (Mitchell et al., 1991, Genes & Dev. 5:105–119) without a demonstrated role in endothelial cell gene regulation. NFκB is thought to trans-activate the inducible expression of vascular cell adhesion molecule-1 and tissue factor in endothelial cells (Iademarco, 1992, J. Biol. Chem. 267:16323–16329; Moll et al., 1995, J. Biol. Chem. 270:3849–3857) and is known to be a mediator of tissue-specific gene regulation (Lenardo et al., 1989, Cell 58:227–229). Nuclear proteins that bind the E-box motif include the basic helix-loop-helix family of trans-acting factors. E-box binding proteins have not been clearly associated with endothelial cell gene expression, although members of this family are critical for proper maturation of many cell types, including skeletal muscle and B lymphocytes (Buskin et al., 1989, Mol. Cell. Bio. 9:2627–2640; Murre et al., 1989, Cell 58:537–544).

Figure 4A:
FIG. 4A is a diagram showing the location of 3' deletion sites in the KDR/flk-1 promoter. Location of deletion sites is shown in relation to consensus sequences for known nuclear proteins.
Figure 4B:
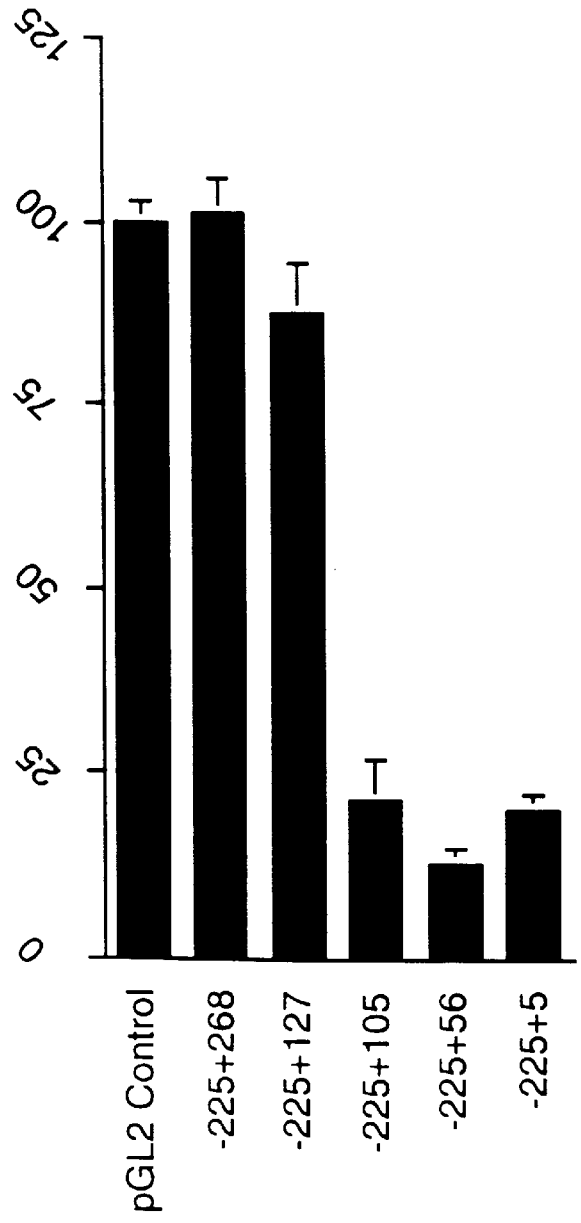
FIG. 4B is a bar graph showing the results of a functional analysis of 3' deletions on KDR/flk-1 promoter activity in BAEC. Luciferase activity is represented as a percentage of pGL2 Control.

To determine whether sequences in the first exon of human KDR/flk-1 are important for basal expression, a series of 3' deletion constructs from the vector pGL2-225+268, which is the smallest construct that possessed full promoter activity, was made (FIGS. 4A and 4B). Deletion of a fragment spanning bp +105 to +127 (SEQ ID NO:4) caused a fivefold reduction in promoter activity (p<0.05), indicating the presence of a positive regulatory element in this region.

The functional importance of the atypical GATA site located between bp +105 and +127 of human KDR/flk-1 was also examined. Three bp of the GATA motif in the fragment −225 to +268 were mutated to GTCG by PCR to create the mutant, pGL2 GATA-MUT. Mutation of these bp in the GATA motif eliminates GATA-2 binding activity in the endothelin-1 gene promoter. In contrast, there was no significant decrease in promoter activity in BAEC with the pGL2 GATA-MUT construct containing the mutated atypical GATA sequence compared to the native pGL2-225+268 promoter construct, (p>0.05; FIG. 5).

Four zinc finger-containing transcription factors in the GATA protein family bind to the consensus sequence (A/T)GATA(A/G) and regulate cell type-specific gene expression in many cell lineages (Orkin, S., 1992, Blood 80:575–581); among these GATA-2 has been most closely linked to endothelial cell gene expression. GATA-2 functions as an enhancer of endothelin-1 gene expression and acts to restrict expression of von Willebrand factor to endothelial cells. Human KDR/flk-1 5' flanking region was found to have two potential GATA-binding sequences, at positions −759 and +107. Loss of the element located at position −759 had no effect on expression of KDR/flk-1 in endothelial cells. The potential GATA element at position +107 is located in a region of the first exon which has now been identified as a powerful positive regulatory element (SEQ ID NO:4). Although this GATA sequence (GGATAT) differs from the GATA-binding sequences of endothelin-1 and von Willebrand factor and from the consensus GATA sequence (A/T)GATA(A/G), the data suggests that it is the functional motif in the region between +105 and +127 because the functional GATA site in the von Willebrand factor gene is located similarly in the first exon, and because a similar GATA element is found in the first exon of the mouse KDR/flk-1 gene. Mutation of three bp in this element (GATA to GTCG), which had been observed to prevent transactivation of the GATA cis-acting element in the endothelin-1 promoter, was found to have no significant effect on KDR/flk-1 promoter activity (FIG. 5). Thus, the deletion analyses and mutagenesis studies do not support a functional role for the two GATA sequences in the human promoter in its high-level activity in endothelial cells. These observations suggest that transcription factors other than GATA proteins are necessary for expression of the human KDR/flk-1 gene.

High-Level Expression Induced by the KDR/flk-1 Promoter Is Specific to Endothelial Cells Although KDR/flk-1 expression is restricted to endothelial cells in vivo, it does not necessarily follow that its expression would be limited to endothelial cells in culture. To determine whether a tissue culture system is suitable for studying cell-type specific regulation of the KDR/flk-1 gene, Northern analysis of RNA extracted from various cells in culture was performed. KDR/flk-1 message was detected in HUVEC but not in primary-culture cells (human aortic and intestinal smooth muscle cells and fibroblasts) or human cell lines (RD, HeLa, HepG2, MCF7, and U937) (see FIGS. 6A and 6B). Similarly, KDR/flk-1 message was not detected by RT-PCR in HeLa, A7r5, or 3T3 cells. Thus, expression of KDR/flk-1 message in tissue culture appears to be restricted to endothelial cells, as it is in vivo.

To determine whether 5' flanking sequences of the KDR/flk-1 gene confer endothelial cell-specific expression in cultured cells, pGL2-4kb+296, which contains over 4 kb of the human KDR/flk-1 5' flanking sequence and includes most of the untranslated portion of the first exon, was transfected into a variety of cell types in culture (FIG. 7). Reporter gene expression driven by the pGL2-4kb+296 promoter fragment was similar to that driven by the potent SV40 promoter/enhancer. In JEG-3, Saos-2, A7r5, 3T3, and HeLa cells, however, expression driven by the pGL2-4kb+296 promoter was markedly lower, demonstrating that induction of high-level expression by these promoter sequences is specific to endothelial cells. A similar expression pattern was observed using a reporter plasmid containing 15.5 kb of KDR/flk-1 5' flanking sequence.

These data indicate that the activity of the KDR/flk-1 promoter in endothelial cells is similar to that of the potent SV40 promoter/enhancer and that this high-level activity is specific to endothelial cells: activity in other cell types is markedly diminished. Low but detectable promoter activity was observed in transient transfection assays of cell types that do not express the KDR/flk-1 gene in vivo; it is possible that other silencer elements outside of the 15.5 kb 5' flanking region are necessary to block promoter activity completely in nonendothelial cells. Alternatively, the context of the promoter in relation to normal chromatin structure may be essential for precise regulation of the gene. The results described above suggest that tissue-specific regulation of KDR/flk-1 involves a complex interaction between known, widely distributed nuclear factors and other, undefined elements.

Use The DNA of the invention promotes endothelial cell-specific transcription of DNA sequences to which it is operably linked. These promoter sequences are useful to direct or prevent the expression of genes specifically in endothelial cells. The invention provides the basis of novel therapeutic approaches to vascular diseases such as arteriosclerosis as well as non-vascular diseases such as cancer, e.g., solid tumors, and inflammatory diseases, e.g., rheumatoid arthritis and diabetic retinopathy, as described in the examples below.

EXAMPLE 1

Gene Therapy

The invention can be used for gene therapy treatment of vascular diseases. The DNA of the invention can be used alone or as part of a vector to express heterologous genes, e.g., genes which encode proteins other than KDR/flk-1, in cells of the blood vessel wall, i.e., endothelial cells, for gene therapy of vascular diseases such as arteriosclerosis. The DNA or vector containing a sequence encoding a polypeptide of interest is introduced into endothelial cells which in turn produce the polypeptide of interest. For example, sequences encoding t-PA (Pennica et al., 1982, Nature 301:214), p21 cell cycle inhibitor (El-Deiry et al., 1993, Cell 75:817–823), or nitric oxide synthase (Bredt et al., 1990, Nature 347:768–770) may be operably linked to the endothelial cell-specific promoter sequences of the invention and expressed in endothelial cells. For example, thrombolytic agents can be expressed under the control of the endothelial cell-specific promoter sequences for expression by vascular endothelial cells in blood vessels, e.g., vessels occluded by aberrant blood clots. Other heterologous proteins, e.g., proteins which inhibit smooth muscle cell proliferation, e.g., interferon-γ and atrial natriuretic polypeptide, may be specifically expressed in endothelial cells to ensure the delivery of these therapeutic peptides to an arteriosclerotic lesion or an area at risk of developing an arteriosclerotic lesion, e.g., an injured blood vessel.

The endothelial cell-specific promoter sequences of the invention may also be used in gene therapy to promote angiogenesis to treat diseases such as peripheral vascular disease or coronary artery disease. For example, the DNA of the invention can be operably linked to sequences encoding cellular growth factors which promote angiogenesis, e.g., VEGF, acidic fibroblast growth factor, or basic fibroblast growth factor.

According to the invention, the DNA of the invention is located sufficiently close to the coding sequence to be transcribed that it functions to direct expression of the polypeptide in an endothelial cell. For example, SEQ ID NO:1, 2, and 3 are preferably located 5' to the transcription start site, and SEQ ID NO:4 is located 3' of the transcription start site. However, these sequences may be in any order relative to the transcription start site provided that endothelial cell-specific promoter activity is preserved.

EXAMPLE 2

Antisense Therapy

The DNA of the invention may also be used in methods of antisense therapy. Antisense therapy may be carried out by administering to an animal, e.g., a human patient, DNA containing the endothelial cell-specific promoter sequences of the invention operably linked to a DNA sequence, i.e., an antisense template, which is transcribed into an antisense RNA. The antisense RNA may a short (generally at least 10, preferably at least 14 nucleotides, and up to 100 or more nucleotides) nucleotide sequence formulated to be complementary to a portion of a specific mRNA sequence. The antisense template is preferably located downstream from the promoter sequences of the invention. A poly A tail is typically located at the end of the antisense sequence to signal the end of the sequence. Standard methods relating to antisense technology have been described (Melani et al., Cancer Res. 51:2897–2901, 1991). Following transcription of the DNA sequence into antisense RNA, the antisense RNA binds to its target mRNA molecules within a cell, thereby inhibiting translation of the mRNA and down-regulating expression of the protein encoded by the mRNA. For example, an antisense sequence complementary to a portion of or all of the KDR-flk-1 mRNA (Terman et al., 1991, Oncogene 6:1677–1683) would inhibit the expression of KDR-flk-1, which in turn would inhibit angiogenesis. Such antisense therapy may be used to treat cancer, particularly to inhibit angiogenesis at the site of a solid tumor, as well as other pathogenic conditions which are caused by or exacerbated by angiogenesis, e.g., inflammatory diseases such as rheumatoid arthritis, and diabetic retinopathy.

The expression of other endothelial cell proteins may also be inhibited in a similar manner. For example, the DNA of the invention can be operably linked to antisense templates which are transcribed into antisense RNA capable of inhibiting the expression of the following endothelial cell proteins: cell cycle proteins (thereby inhibiting endothelial cell proliferation, and therefore, angiogenesis); coagulation factors such as von Willebrand factor; and endothelial cell adhesion factors, such as ICAM-1 and VCAM-1 (Bennett et al., 1994, J. Immunol. 152:3530–3540).

For gene therapy or antisense therapy, the claimed DNA may be introduced into target cells of an animal, e.g., a patient, using standard vectors and/or gene delivery systems. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy or antisense therapy may also be accomplished using a biolistic delivery system, such as that described by Williams et al., 1991, Proc. Natl. Acad. Sci. U.S.A. 88:2726–2729. Standard methods for transfecting cells with isolated DNA are well known to those skilled in the art of molecular biology. Gene therapy and antisense therapy to prevent or decrease the development of arteriosclerosis or inhibit angiogenesis may be carried out by directly administering the claimed DNA to a patient or by transfecting endothelial cells with the claimed DNA ex vivo and infusing the transfected cells into the patient.

DNA or transfected cells may be administered in a pharmaceutically acceptable carrier. Pharmaceutically acceptable carriers are biologically compatible vehicles which are suitable for administration to an animal, e.g., physiological saline. A therapeutically effective amount is an amount of the DNA of the invention which is capable of producing a medically desirable result in a treated animal. As is well known in the medical arts, dosages for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{22}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery.

OTHER EMBODIMENTS

In addition to antisense therapy for inhibition of angiogenesis, expression of KDR/flk-1 in endothelial cells can also be carried out by inhibiting the binding of transcription factors, e.g., AP-2, SP-1 and NFκB, to the cis-acting binding sites in the promoter sequences of the invention. For example, transcription can be inhibited using dominant negative mutants of transcription factors, e.g., a dominant negative mutant of AP-2 which binds to the AP-1 binding site but fails to activate transcription. Alternatively, compounds which downregulate production of transcription factors, e.g., retinoic acid or dexamethasone which downregulate production of AP-2 and NFκB, can be administered to inhibit angiogenesis by inhibiting expression of KDR/flk-1.

---

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
  ( A ) LENGTH: 62 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:1:

```
TTGTTGCTCT GGGATGTTCT CTCCTGGGCG ACTTGGGGCC CAGCGCAGTC CAGTTGTGTG      60

GG                                                                    62
```

( 2 ) INFORMATION FOR SEQ ID NO:2:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:2:

```
GCTGGCCGCA CGGGAGAGC                                                  19
```

( 2 ) INFORMATION FOR SEQ ID NO:3:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:3:

```
GCTGGCCGCA CGGGAGAGCC CCTCCTCCGC CCCGGC                               36
```

( 2 ) INFORMATION FOR SEQ ID NO:4:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:4:

```
GGATATCCTC TCCTACCGGC AC                                              22
```

( 2 ) INFORMATION FOR SEQ ID NO:5:

( i ) SEQUENCE CHARACTERISTICS:
    ( A ) LENGTH: 493 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:5:

```
TTGTTGCTCT GGGATGTTCT CTCCTGGGCG ACTTGGGGCC CAGCGCAGTC CAGTTGTGTG      60

GGGAAATGGG GAGATGTAAA TGGGCTTGGG GAGCTGGAGA TCCCCGCCGG GTACCGGGT      120

GAGGGGCGGG GCTGGCCGCA CGGGAGAGCC CCTCCTCCGC CCCGGCCCCG CCCCGCATGG     180

CCCCGCCTCC GCGCTCTAGA GTTTCGGCTC CAGCTCCCAC CCTGCACTGA GTCCCGGGAC     240
```

```
CCCGGGAGAG  CGGTCAGTGT  GTGGTCGCTG  CGTTTCCTCT  GCCTGCGCCG  GGCATCACTT    300

GCGCGCCGCA  GAAAGTCCGT  CTGGCAGCCT  GGATATCCTC  TCCTACCGGC  ACCCGCAGAC    360

GCCCCTGCAG  CCGCCGGTCG  GCGCCCGGGC  TCCCTAGCCC  TGTGCGCTCA  ACTGTCCTGC    420

GCTGCGGGGT  GCCGCGAGTT  CCACCTCCGC  GCCTCCTTCT  CTAGACAGGC  GCTGGGAGAA    480

AGAACCGGCT  CCC                                                          493
```

( 2 ) INFORMATION FOR SEQ ID NO:6:

( i ) SEQUENCE CHARACTERISTICS:
    ( A ) LENGTH: 352 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:6:

```
TTGTTGCTCT  GGGATGTTCT  CTCCTGGGCG  ACTTGGGGCC  CAGCGCAGTC  CAGTTGTGTG     60

GGGAAATGGG  GAGATGTAAA  TGGGCTTGGG  GAGCTGGAGA  TCCCCGCCGG  GTACCCGGGT    120

GAGGGGCGGG  GCTGGCCGCA  CGGGAGAGCC  CCTCCTCCGC  CCCGGCCCCG  CCCCGCATGG    180

CCCCGCCTCC  GCGCTCTAGA  GTTTCGGCTC  CAGCTCCCAC  CCTGCACTGA  GTCCCGGGAC    240

CCCGGGAGAG  CGGTCAGTGT  GTGGTCGCTG  CGTTTCCTCT  GCCTGCGCCG  GGCATCACTT    300

GCGCGCCGCA  GAAAGTCCGT  CTGGCAGCCT  GGATATCCTC  TCCTACCGGC  AC            352
```

( 2 ) INFORMATION FOR SEQ ID NO:7:

( i ) SEQUENCE CHARACTERISTICS:
    ( A ) LENGTH: 1267 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:7:

```
CCTCCTTCCC  CTGGGCCTAA  GGATATCTTG  GCTGGAAGCT  CTGCTCTGAA  AAGGGGCATG     60

GCCAAACTTT  CACTAGGGCT  CTTCGTTGGG  GAGCACGATG  GACAAAAGCC  TTCTTGGGGC    120

TAGGCAGGTC  ACTTCAAACT  TGGAGCCGCC  AAATATTTTG  GGAAATAGCG  GGAATGCTGG    180

CGAACTGGGC  AAGTGCGTTT  TCTGATTAAG  AGCAACCAGA  TTCAGCTTTT  TAAACTACAA    240

TTATACTGGC  CAAACAAAAT  ACCCTTATAC  AAAAACCAAA  ACTACTGGCA  GGAGTCGCTG    300

CCAGCTTGCG  ACCCGGCATA  CTTGGCTGAG  TATCCGCTTC  TCCCTTGTGG  CTGGAAACTG    360

ATGCAGATTC  TCGGCCACTT  CAGACGCGCG  CGATGGCGAA  GAGGGTCCTG  CACTTTGACG    420

CGCCTGGTGA  GGGAGCGGTG  CTCTTCGCAG  CGCTCCTGGT  GATGCTCCCC  AAATTTCGGG    480

GACCGGCAAG  CGATTAAATC  TTGGAGTTGC  TCAGCGCCCG  TTACCGAGTA  CTTTTTATTT    540

ACACCAGAAA  CAAAGTTGTT  GCTCTGGGAT  GTTCTCTCCT  GGGCGACTTG  GGCCCAGCG     600

CAGTCCAGTT  GTGTGGGGAA  ATGGGGAGAT  GTAAATGGGC  TTGGGGAGCT  GGAGATCCCC    660

GCCGGGTACC  CGGGTGAGGG  GCGGGGCTGG  CCGCACGGGA  GAGCCCTCC   TCCGCCCGG    720

CCCCGCCCCG  CATGGCCCCG  CCTCCGCGCT  CTAGAGTTTC  GGCTCCAGCT  CCCACCCTGC    780

ACTGAGTCCC  GGGACCCCGG  GAGAGCGGTC  AGTGTGTGGT  CGCTGCGTTT  CCTCTGCCTG    840

CGCCGGGCAT  CACTTGCGCG  CCGCAGAAAG  TCCGTCTGGC  AGCCTGGATA  TCCTCTCCTA    900

CCGGCACCCG  CAGACGCCCC  TGCAGCCGCC  GGTCGGCGCC  CGGGCTCCCT  AGCCCTGTGC    960
```

```
GCTCAACTGT  CCTGCGCTGC  GGGGTGCCGC  GAGTTCCACC  TCCGCGCCTC  CTTCTCTAGA    1020

CAGGCGCTGG  GAGAAAGAAC  CGGCTCCGA   GTTCTGGGCA  TTTCGCCCGG  CTCGAGGTGC    1080

AGGATGCAGA  GCAAGGTGCT  GCTGGCCGTC  GCCCTGTGGC  TCTGCGTGGA  GACCCGGGCC    1140

GCCTCTGTGG  GTAAGGAGCC  CACTCTGGAG  GAGGAAGGCA  GACAGGTCGG  GTGAGGGCGG    1200

AGAGGACCTG  AAAGCCAGAT  CTAACTCGGA  ATCGTAGAGC  TGGAGAGTTG  GACAGGACTT    1260

GACATTT                                                                   1267
```

(2) INFORMATION FOR SEQ ID NO:8:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
ACTTCTACCA  GAAACCGAGC  TGCGTCCAGA  TTTGCTCTCA  GATGCGACTT  GCCGCCCGGC     60

ACAGTCCGGG  GTAGTGGGGG  AGTGGGCGTG  GGAAACCGGG  AAACCCAAAC  CTGGTATCCA    120

GTGGGGGGCG  TGGCCGGACG  CAGGGAGTCC  CCACCCCTCC  CGGTAATGAC  CCCGCCCCCA    180

TTCGCTAGTG  TGTAGCCGGC  GCTCTCTTTC  TGCCCTGAGT  CCTCAGGACC  CCAAGAGAGT    240

AAGCTGTGTT  TCCTTAGATT  CGGGGACCGC  TACCCGGCAG  GACTGAAAGC  CCAGACTGTG    300

TCCCGCAGCC  GGGATAACCT  GGCTGACCCG  ATTCCGCGGA  CACCGCTGCA  GCCGCGGCTG    360

GAGCCAGGGC  GCCGGTGCCC  CGCGCTCTCC  CCGGTCTTGC  GAAGGAGTCT  GTGCCTGAGA    420

AACTGGGCTC  TGTGCCCAGG  CGCGAGGTGC  AGGATGGAGA  GCAAGGCGCT  GCTAGCTGTC    480

GCTCTGTGGT  TCTGCGTGGA                                                    500
```

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
CTGTCTAGAG  AAGGAGGCGC  GGAGGTGGAA  CT                                     32
```

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TCTGGCAGCC  TGGTCGTCCT  CTCCTA                                             26
```

(2) INFORMATION FOR SEQ ID NO:11:

(i) SEQUENCE CHARACTERISTICS:
        (A) LENGTH: 26 base pairs
        (B) TYPE: nucleic acid (C) STRANDEDNESS: single
(D) TOPOLOGY: linear (ii) MOLECULE TYPE: DNA (xi) SEQUENCE DESCRIPTION: SEQ ID NO:11:

TAGGAGAGGA CGACCAGGCT GCCAGA 26

(2) INFORMATION FOR SEQ ID NO:12:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

TGCCTCGAGT TGTTGCTCTG GGATGTT 27

(2) INFORMATION FOR SEQ ID NO:13:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

TGTAAGCTTG GGAGCCGGTT CTTTCTC 27

(2) INFORMATION FOR SEQ ID NO:14:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

CCCTGCACTG A 11

(2) INFORMATION FOR SEQ ID NO:15:

(i) SEQUENCE CHARACTERISTICS:
(A) LENGTH: 22 amino acids
(B) TYPE: amino acid
(D) TOPOLOGY: linear (ii) MOLECULE TYPE: protein (xi) SEQUENCE DESCRIPTION: SEQ ID NO:15:

Met Gln Ser Lys Val Leu Leu Ala Val Ala Leu Trp Leu Cys Val Glu
 1               5                  10                  15
Thr Arg Ala Ala Ser Val
                20

(2) INFORMATION FOR SEQ ID NO:16:

(i) SEQUENCE CHARACTERISTICS:
(A) LENGTH: 16 amino acids
(B) TYPE: amino acid
(D) TOPOLOGY: linear -continued ( i i ) MOLECULE TYPE: protein ( x i ) SEQUENCE DESCRIPTION: SEQ ID NO:16:

| Met | Glu | Ser | Lys | Ala | Leu | Leu | Ala | Val | Ala | Leu | Trp | Phe | Cys | Val | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Other embodiments are within the following claims.

What is claimed is:

1. A substantially pure DNA comprising a first DNA sequence consisting of SEQ ID NO:6, operably linked to a second DNA sequence encoding a polypeptide other than KDR/flk-1, wherein said first DNA sequence directs a higher level of transcription of said second DNA sequence when introduced in an endothelial cell compared to when introduced in a non-endothelial cell.

2. A substantially pure DNA comprising a first DNA sequence consisting of SEQ ID NO:7, operably linked to a second DNA sequence encoding a polypeptide other than KDR/flk-1, wherein said first DNA sequence directs a higher level of transcription of said second DNA sequence when introduced in an endothelial cell compared to when introduced in a non-endothelial cell.

3. A substantially pure DNA comprising a first DNA sequence consisting of SEQ ID NO:5, operably linked to a second DNA sequence encoding a polypeptide other than KDR/flk-1, wherein said first DNA sequence directs a higher level of transcription of said second DNA sequence when introduced in an endothelial cell compared to when introduced in a non-endothelial cell.

4. The DNA of claim 1, wherein said polypeptide is chosen from a group consisting of tissue plasminogen activator, p21 cell cycle inhibitor, nitric oxide synthase, interferon-γ, and atrial natriuretic polypeptide.

5. A vector comprising the DNA of claim 1.

6. A method of directing expression of a polypeptide in a cultured endothelial cell, comprising introducing into said endothelial cell the rector of claim 5, wherein said first DNA sequence directs a higher level of expression of said polypeptide when introduced in said endothelial cell compared to when introduced in a non-endothelial cell.

7. An isolated endothelial cell comprising the vector of claim 5.

8. A substantially pure DNA comprising a first DNA consisting of SEQ ID NO:6, operably linked to a second DNA sequence which is an antisense template the transcript of which is complementary to a portion of an mRNA encoding an endothelial cell polypeptide, wherein said first DNA sequence directs a higher level of transcription of said second DNA sequence when introduced in an endothelial cell compared to when introduced in a non-endothelial cell.

9. The DNA of claim 8, wherein said endothelial cell polypeptide is KDR/flk-1.

10. The DNA of claim 8, wherein said endothelial cell polypeptide is chosen from a group consisting of a cell cycle protein, a coagulation factor and a cell adhesion factor.

* * * * *